US005814316A

United States Patent [19]
Cook et al.

[11] Patent Number: 5,814,316
[45] Date of Patent: Sep. 29, 1998

[54] COMPOUND TO MIMICK A NATURALLY OCCURRING PEPTIDE'S EFFECT

[75] Inventors: Mark E. Cook; Cheryl C. Miller, both of Madison, Wis.; Julio L. Pimentel, Buford, Ga.

[73] Assignee: Wisconsin Alumni Research Foundation, Madison, Wis.

[21] Appl. No.: 286,113

[22] Filed: Aug. 5, 1994

[51] Int. Cl.⁶ .................. A61K 39/395; A61K 39/40; A61K 39/42
[52] U.S. Cl. .................. 424/139.1; 424/130.1; 424/145.1; 424/158.1; 530/328; 530/387.9
[58] Field of Search ............ 424/130.1, 139.1, 424/145.1, 158.1; 530/328, 387.9

[56] References Cited

U.S. PATENT DOCUMENTS

| 4,748,018 | 5/1988 | Stolle et al. ................ 424/87 |
| 5,080,895 | 1/1992 | Tokoro .................. 424/85.8 |

FOREIGN PATENT DOCUMENTS

| 339549 | 2/1989 | European Pat. Off. . |
| WOA9219253 | 12/1992 | WIPO . |
| 05311 | 3/1994 | WIPO . |

OTHER PUBLICATIONS

"Cholecystokinin–Octapeptidelike Immunoreactivity in Human Plasma", Walsh et al, Gastroenterology, Mar., 1982, vol. 82, pp. 438–444.
"Effect of CCK Antibodies on Food Intake & Weight Gain in Zucker Rats" McLaughlin et al, Physiology & Behavior, 1985, vol. 34, pp. 277–282.
"USDA, biotech firm develop compound to get pigs to eat", Muirhead, Feedstuffs, May 22, 1989.
"Gastric Stimulation by Intravenous Injection of Cholecystokinin and Secretin in Fistula Chickens", Burhol, Scand.J. Gastroent, 1974, pp. 49–53.
"Recent Studies on Regulation of Gastric Motlility in Turkeys", Duke, World's Poultry Science Association Invited Lecture, 1991, pp. 1–9.
Influence of Vagotomy in Domestic Fowls on Feeding Activity, Food Passage, Digestibility and Satiety Effects of Two Peptides, Savory et al, Physiology & Behavior, 1984, vol. 33, pp. 937–944.
"Effect of Cholecystokinin Immunization, Enhanced Food Intake and Growth of Swing on Lean Yield and Carcass Composition", Jerome C. Pekas, American Institute of Nutrition, 1990, pp. 563–567.
"Are there Hunger and Satiety Factors in the Blood of Domestic Fowls?", Savory et al, Academic Press, Inc., 1987, pp. 101–110.
"The New Wonders of Barnyard Biotechnology", George Sollenberger, The Furrow, Corn Belt Edition, Jan.–Feb., 1994, p. 9–13.
"Cholecystokinin Octapeptide Immunization: Effect on Growth of Barrows and Gilts", Pekas et al, J. Anim. Sci., 1993, vol. 71, pp. 2499–2505.

"Influence of Intravenous Injections of Cholecystokinin on Gastrointestinal Motility in Turkeys and Domestic Fowls", Savory et al, Biochem. Physiol., 1981, vol. 70A, pp. 179–189.
"Cholecystokinin Decreases Food Intake In Rats", Gibbs et al, Journal of Comparative and Physiology, 1973, vol. 84, No. 3, pp. 489–495.
"Immune, Growth And Carcass Responses Of Ram Lambs To Active Immunization Against Desulfated Cholecystokinin (CCK–8)", Trout et al, J. Anim. Sci., 1989, vol. 67, p. 2709–2714.
"Immunization Against Cholecystokinin Decreases Appetite in Lambs", Spencer, J. Anim. Sci., 1992, vol. 70, p. 3820–3824.
"Stimulation of Food Intake and Growth of Swine by Cholecystokinin Immunization", Pekas et al, Growth, Development & Aging, 1990, vol. 54, pp. 51–56.
"Hormones and feed intake", Baile et al, Proc. Nutr. Soc., 1983, vol. 42, pp. 113–127.
"Gastrin", John H. Walsh, Gut Peptides: Biochemistry and Physiology, 1994, pp. 75–76.
"Nutrition of the Chicken", Scott et al, M.L. Scott & Associates, Second Edition, 1976, pp. 435–437.
"Utilisation of Raw Jackbean (Canavalia Ensiformis) And Jackbean Fractions In Diets For Broiler Chicks", Ologhobo et al, British Poultry Science, 1993, vol. 34, pp. 323–337.
"Toxicity of Raw Limabeans (Phaseolus Lunatus L.) And Limabean Fractions for Growing Chicks", Ologhobo et al, British Poultry Science, 1993, vol. 34, pp. 505–522.
"Microwave treated whole soybeans as a feedstuff in poultry diets", John C. Fuller, Jr., A Thesis Submitted to the Graduate Faculty in Partial Fulfillment of the Requirements for the Degree of Master Of Science, Iowa State University, Ames, Iowa, 1985, pp. 1–13.
"Influence of Heat And Supplementation With Methionine On The Nutritive Value Of Soybean Protein", Evans et al, J. Nutr., 31, 449, 1946, as it appears in Handbook of Nutritive Value of Processed Food, vol. II, Animal Feedstuffs, p. 327–330.
"Relationships Between Color, Trypsin Inhibitor Contents, and Urease Index of Soybean Meal and Effects on Broiler Performance", McNaughton et al, Poultry Science, 1981, vol. 60, pp. 393–400.

(List continued on next page.)

*Primary Examiner*—Sheela Huff
*Attorney, Agent, or Firm*—Andrus, Sceales, Starke & Sawall

[57] ABSTRACT

The novel compound which is the reverse amino acid sequence of a naturally occurring peptide will elicit an immune response when introduced into an organism. Antibodies raised to this reverse compound act as antagonist to the naturally occurring peptide thereby mimicking the natural peptide's physiological effect on the organism's system. Precisely, antibodies specific to reverse choleocystokinin elicit the same response in avians and mammals as naturally occurring choleocystokinin, that being an increase in satiety and a decrease in food consumption.

18 Claims, No Drawings

OTHER PUBLICATIONS

"Effects of Heat Treatment on the Nutritional Value of Conventional and Low Trypsin Inhibitor Soybeans for Chicks", Herkelman et al, Poultry Science, 1993, vol. 72, p. 1359–1369.

The Merck Index, Eleventh Edition, 1989, pp. 341 and 1352.

"Cholecystokinin", Annals Of The New York Academy of Sciences, 1994, vol. 713, pp. 12 and 33.

"Neutrotransmitters and Neuromodulators", Gainer of Brownstein, 1981, pp. 164–167.

Gut Peptides, Biochemistry and Physiology, Raven Press, New York (1992) Table of Contents Only.

Organic Chemistry, 4th Edition, Morrison et al, pp. 787, 789, 799, 825–826 (1983).

"Molecular Design of Life", Biochemistry, 3rd Edition, p. 22 (1988).

Biochemicals, Organic Compounds, Diagnostic Reagents, SIGMA product order list (1992).

"Intravenous Injections of Cholecystrokinin and Caerulein Suppress Food Intake in Domestic Fowls", Savory et al, 1980, Experientia 36.

COMPOUND TO MIMICK A NATURALLY OCCURRING PEPTIDE'S EFFECT

BACKGROUND OF THE INVENTION

An elaborate cell to cell communication network coordinates the growth, differentiation, and metabolism of the multitude of cells in the diverse tissues and organs that make up all mammals and avians. Within small groups of cells, communication is often by direct cell—cell contacts. Gap junctions permit these adjacent cells to exchange small molecules and coordinate metabolic responses. Moreover, the establishment of specific contacts between different types of cells is a necessary step in the differentiation of many tissues.

However, cells also have to communicate over distances longer than those facilitated by cell—cell contacts. For this purpose, extracellular substances act as signals. A substance released by the signaling cell is recognized by the target cell, in which the substance induces a specific response. Cells use an enormous variety of chemicals and signaling mechanisms to communicate with each other, many of which are peptides including many hormones and neurotransmittors. Choleocystokinin and gastrin are two examples of peptides which function as hormones. Many neuropeptides function as neurotransmittors such as beta-endorphin and somatostatin. Most signaling molecules that induce cellular responses bind to receptors on the target cell's plasma membrane. On the surface of the target cell are receptor proteins that have binding sites with a high affinity for particular signaling substances such as a hormone or a neuropeptide. These signaling substances, commonly referred to as ligands, bind to or "fit" a receptor site. When the ligand binds to the receptor, the receptor-ligand complex initiates a sequence of reactions that changes the function of a cell. Specifically, binding triggers an increase or decrease in the cytosolic concentration of cyclic AMP (cAMP), calcium or some other substance. Often the target cells modify or degrade the ligand thereby terminating the response to the signal. The calcium or cAMP acts within a cell as a second messenger. The elevated intercellular concentration of either of these two substances triggers a rapid alteration in the activity of one or more enzymes or non-enzymatic proteins resulting in a physiological phenomena in the organism as a whole. This type of reaction allows the cell, and thus physiological systems, to respond quickly to a stimuli.

There exists chemically synthesized analogs of natural molecules which are able to bind to cell surface receptors. These analogs fall into two classes: (1) agonists that mimick the molecule function, binding to the receptor and causing the normal response; and (2) antagonists that bind to the receptor but do not activate the molecule's induced function. A bound antagonist competes with the binding of the natural molecule or the agonist and blocks the physiological activity.

The inventors have discovered that antibodies to a "reverse peptide" act as agonist to the natural peptide thereby mimicking the natural peptide's function by binding to the receptor and causing the natural peptide's normal physiological response. Reverse peptides are synthetic peptides in which the amino to carboxyl amino acid sequence is the exact reverse of the amino to carboxyl sequence of the naturally occurring peptide or protein. The inventors have found that antibodies to these reverse peptides have secondary or tertiary structures which recognize the same cell receptors as the original protein. These antibodies are able to bind to these same cell receptors and induce the same bioregulatory response. Specifically, the inventors discovered this phenomena using a reverse choleocystokinin peptide.

Choleocystokinin, or CCK, is an octapeptide hormone that has been shown to negatively affect food intake and thus inhibit growth in both mammals (Gibbs et al, 1973) and birds (Savory and Hodgkiss, 1984). Antibodies to naturally occurring CCK peptide have been successfully produced endogenously in pigs (Pekas and Trout, 1990; Pekas 1991) and rats (MacLaughlin et al, 1985). In both species, feed consumption is decreased upon introduction of the naturally occurring peptide and prevented with the use of CCK antibodies.

The effects of CCK in animals is well known. CCK represents a polypeptide hormone which is released when food enters the small intestine. The presence of CCK in the gut lumen alters gastrointestinal (GI) motility. CCK, which is normally released after a meal is consumed, controls the rate in which food travels through the intestine by causing an increase in intestinal contraction.

The presence of CCK also alters the willingness to eat. CCK is responsible for what is known as the satiety effect which is a physiological effect that sharply decreases an animal's appetite.

SUMMARY OF THE INVENTION

This invention relates to using antibodies to reverse peptides in order to mimick the physiological effect of the original or naturally occurring protein. Specifically, the inventors have found that when antibodies to the reverse CCK peptide are fed or directly transferred (i.e. via passive immunoglobulin transfer from dam to offspring or through injection of the antibody) to avians or mammals, the physiological result obtained is the same as the CCK peptide itself. Thus, the organism experiences a satiated feeling and a reduction in feed consumption.

The reverse CCK protein acts as an antigen. An antigen is simply a substance that when introduced into an animal with a functioning immune system, can elicit a specific immune response. Specifically, the immune response involves production of antibodies in the circulation specific to the reverse CCK protein. The antibody raised to this novel compound "resembles" natural CCK and therefore it binds to the cell receptors for CCK. In doing so the circulating reverse CCK antibodies cause an increase in satiety and subsequent decrease in food consumption.

The effect of the reverse peptide antibody mimicking the original peptide's physiological function can be achieved by:

(1) direct transfer (injection) of the reverse antibody; (2) direct transfer (injection) of the reverse peptide (i.e. stimulation of endogenous reverse antibody); (3) passive transfer from the dam to her offspring of reverse antibody and (4) upon feeding harvested reverse antibody.

One method in which an immune response is achieved via inoculation involves injecting an animal with a reverse peptide resulting in that animal producing antibodies specific to the reverse peptide. These reverse antibodies can be isolated and subsequently injected into a second animal. Soon after injection, the second animal shows the same effect as if the original peptide was released naturally in its system.

Secondly, the reverse peptide itself can be injected resulting in the inoculated animal raising reverse peptide antibodies.

Thirdly, a dam whose system has been stimulated to produce endogenous reverse antibodies can pass these antibodies to her offspring.

Lastly, this invention relates to a specific antibody containing substance produced from an animal immunized against a selected antigen. The substance is mixed with feed and subsequently fed to poultry or livestock to elicit an immune response. The antibodies can be isolated from the immunized animal's blood, or more practically, from the animal's by-products such as eggs or milk.

The feeding transfer can be illustrated in avians and mammals using the reverse CCK peptide. First, laying hens are injected with reverse CCK and subsequently antibodies specific to reverse CCK are produced. The reverse CCK specific antibodies are passed to the yolk, harvested from the yolk or fed as dried yolk, and used as a feed additive. Avians or mammals which consume this treated feed show a decline in feed consumption.

There are many advantages to this invention speciftcally when the CCK is the target peptide. This reverse CCK product could have tremendous commercial potential as a human diet therapeutic. Ordinarily to achieve weight loss, an individual must lower calorie intake by eating less food in general, especially food with a high fat and calorie content. Dietary programs which aid overweight individuals are time consuming and extremely expensive. Individuals must sustain the willpower to eat less and in many instances simple willpower is not enough. This invention will reduce food intake without requiring any mental determination. In short, the method cannot fail due to a subject who cannot control poor eating habits.

Another method of weight loss in humans is via surgery. There are two main types: (1) intestinal by-pass surgery; and (2) stomach "stapling". Intestinal by-pass surgery results in less time for food to be absorbed in the intestinal tract. Stomach stapling is a surgery which results in a decrease in stomach size allowing the individual to eat only small portions. As with any surgery there are many risks to these procedures such as the danger of an adverse reaction to anesthetics or other pharmaceuticals employed. There is also the possibility of scarring and infection. The anxiety and pain associated with major surgery must be accounted for as well as the high cost and inconvenience. The reverse CCK administration overcomes all of these substantial shortcomings.

Additionally, since the antibody is a naturally produced peptide, no side effects are expected. Thus, the CCK antibody is safer than using synthetic drugs or chemical compounds in order to control appetite.

Since the physiological effect of administering the reverse antibody was found to be reversible, its effects are not residual. Thus, when the administration of the antibody stops, the effects also cease.

In a general sense, a reverse peptide or reverse antibody could be used as a vaccine in individuals who are defective in the natural production of a peptide or hormone.

DETAILED DESCRIPTION OF THE PREFERRED EMBODIMENT

There are three modes in eliciting an immune response to reverse CCK in mammals or poultry: (1) direct transfer (injection) of the reverse CCK antibody; (2) direct transfer (injection) of the reverse CCK peptide (i.e. stimulation of endogenous reverse CCK antibody); (3) passive transfer from dam to offspring of reverse CCK antibody; and (4) upon feeding harvested reverse CCK antibodies.

The first mode of this invention involves direct transfer of the reverse CCK antibody to an animal. This involves injecting an animal with reverse CCK peptide and, as a result, this animal produces antibodies specific to reverse CCK. These reverse antibodies can be isolated and subsequently injected into a second animal. This second animal shows an immune response consisting of the animal feeling satiated and consuming less food.

The second mode of this invention which relates to direct transferring of reverse CCK peptide involves injecting an animal with reverse CCK peptide and, as a result, the animal raises antibodies specific to reverse CCK thereby eliciting an immune response consisting of the animal feeling satiated and consuming less food.

The third mode of this invention involves passive transfer of reverse CCK antibodies from a dam to her offspring. The dam could be stimulated in a number of ways in order to sufficiently produce and transfer antibodies to her progeny. The dam can be inoculated with either reverse CCK peptide or reverse CCK antibody. Additionally, the dam could be fed reverse CCK antibodies.

The fourth mode of this invention involves orally feeding CCK antibody produced from a reverse CCK immunized animal. Specifically, the CCK antibody could be derived from milk, whole blood, serum, plasma or eggs. Specifically, the eggs of a reverse CCK vaccinated hen could be used. The reverse CCK antibody containing eggs are prepared and mixed into animal meal. Avian or mammals which consume this antibody containing meal soon show an immune response specific to reverse CCK. Human foodstuff could also contain an effective amount of reverse CCK antibody. This appears to be the most commercially viable of all four modes.

The backwards or reverse CCK peptide amino acid sequence is as follows:

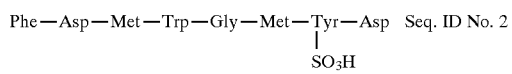
Phe—Asp—Met—Trp—Gly—Met—Tyr—Asp   Seq. ID No. 2
                                              |
                                            SO₃H The CCK peptide amide amino acid sequence is as follows:

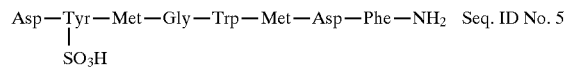
Asp—Tyr—Met—Gly—Trp—Met—Asp—Phe—NH₂   Seq. ID No. 5
      |
    SO₃H

The synthesis of the reverse peptide is accomplished using standard procedures for peptide synthesis. The production of reverse CCK antibody for oral administration can be done by utilizing known technology for producing antibodies in egg yolks. In that process, hens are challenged by injecting them with reverse CCK. In response to exposure to the reverse CCK antigen, the eggs laid by these hens contain high levels of reverse CCK antibody in the yolk. Automated system separate and spray dry the yolks into a powder. The yolks can alternatively be lyophilized. This standard technique is well established in the art for producing various antibodies for other purposes (e.g. diagnoses, resistance to pathogens, etc.)

Whole eggs may be used and it is therefore not necessary to separate the yolk from the albumen. Typically, 0.1 to one reverse CCK antibody containing egg is used per 8 pounds of feed. However, in some uses, as much as 10 eggs per pound of food may be needed. The number of eggs needed depends on the ability of getting high antibody titer. In some situations it is less expensive to use minimal methods in increasing antibody level (i.e., fewer antigen boasts), since the labor costs associated with additional vaccinations is high relative to egg costs. In other situations, very high titers are required to maximize the antibody level in the eggs such that the amount of antibody containing product that would have to be added to an organic food product would be minimal.

Chickens are the most preferable source of eggs but can be substituted with turkeys, geese, ducks and the like.

The reverse CCK should be conjugated with a carrier or foreign protein for use as the antigen. Reverse CCK alone has a molecular weight of only 1,143 Daltons. In order to invoke an immune response, a molecular weight of approximately 10,000 Daltons is required. Therefore, the reverse CCK peptide should be conjugated with a carrier protein with a molecular weight of at least approximately 8,000 Daltons in order for the conjugate to elicit an immune response. Carriers include a wide variety but commonly entail bovine gamma globulin or keyhole limpet hemocyanin.

The reverse CCK peptide conjugated to its carrier protein is injected into the target animal with a common adjuvant. The CCK-carrier conjugate can be emulsified in Freund's complete adjuvant, for example. If mammals are the target animals, then subsequent inoculations should consist of incomplete adjuvant.

Any peptide which successfully and specifically binds to CCK receptors and elicits the effects of increased satiety and decreased food consumption will be acceptable as a functional analog to CCK invention.

METHOD I

The reversed CCK was conjugated to bovine gamma-globulin (IgG) using the glutaraldehyde conjugation procedure, and emulsified in either Freund's complete (primary inoculation) or incomplete adjuvant (secondary inoculation). Each of approximately 96 Single Comb White Leghorn Hens were injected with 100ug/hen of the reversed CCK conjugated with an equal quantity of bovine IgG. The immunization was repeated 7 days after the primary injection.

Egg yolks were pooled from the immunized and non-immunized hens, freeze dried, ground and used in a chick feeding study.

Six pens of 5 chicks were assigned to one of the following three treatments:

(1) Control—5 control yolks/3.64 kg feed;

(2) Low Yolk—1 reversed CCK antibody containing yolk/3.64 kg feed;

(3) High Yolk—5 reversed CCK antibody containing yolks/3.64 kg feed.

TABLE I

EFFECT OF FEEDING EGG YOLK ANTIBODIES TO REVERSED CCK ON THE BODY WEIGHT GAIN OF BROILER CHICKS
(mean + std error)

| Treatment | $n^1$ | 0–5 | 0–11 | 0–14 | 0–21 |
|---|---|---|---|---|---|
| Control* | 6 | 50 ± 2 | 185 ± 8 | 274 ± 10 | 596 ± 15 |
| Low Yolk** | 6 | 46 ± 1 | 165 ± 6 | 260 ± 9 | 571 ± 16 |
| High Yolk*** | 6 | 44 ± 3 | 158 ± 7 | 258 ± 11 | 543 ± 19 |

*11 grams dried control egg yolk per kg diet
**2.45 grams dried CCK invert antibody yolk per kg diet
***12 grams dried CCK invert antibody yolk per kg diet
$^1$6 pens of 5 chicks

TABLE II

EFFECT OF FEEDING EGG YOLK ANTIBODIES TO REVERSED CCK ON BROILER CHICK FEED CONSUMPTION
(mean + std error)

| Treatment | $n^1$ | 0–5 | 0–11 | 0–14 | 0–21 |
|---|---|---|---|---|---|
| Control* | 6 | 70 ± 2 | 274 ± 6 | 440 ± 12 | 905 ± 23 |
| Low Yolk** | 6 | 77 ± 2 | 270 ± 8 | 428 ± 9 | 881 ± 24 |
| High Yolk*** | 6 | 75 ± 3 | 254 ± 9 | 404 ± 12 | 833 ± 26 |

*11 grams dried control egg yolk per kg diet
**2.45 grams dried CCK invert antibody yolk per kg diet
***12 grams dried CCK invert antibody yolk per kg diet
$^1$6 pens of 5 chicks

TABLE III

EFFECT OF FEEDING EGG YOLK ANTIBODIES TO REVERSED CCK ON THE FEED CONVERSION (FEED CONSUMED/GAIN) OF BROILER CHICKS
(mean + std error)

| Treatment | $n^1$ | 0–5 | 0–11 | 0–14 | 0–21 |
|---|---|---|---|---|---|
| Control* | 6 | 1.57 ± .02 | 1.49 ± .03 | 1.55 ± .01 | 1.52 ± .01 |
| Low Yolk** | 6 | 1.66 ± .03 | 1.64 ± .06 | 1.60 ± .01 | 1.58 ± .01 |
| High Yolk*** | 6 | 1.69 ± .05 | 1.62 ± .02 | 1.55 ± .04 | 1.54 ± .02 |

*11 grams dried control egg yolk per kg diet
**2.45 grams dried CCK invert antibody yolk per kg diet
***12 grams dried CCK invert antibody yolk per kg diet
$^1$6 pens of 5 chicks

METHOD II

Hen feed intake was measured 25 days after the primary inoculation over a 24 hour period. It was found that on average the hens were consuming only 50% of the feed consumed by non-inoculated hens. It was found that 5/12 of the reversed CCK inoculated hens did not consume feed during this period of time as compared to 0/12 of the control hens. See Tables IV and V for results.

TABLE IV

EFFECT OF IMMUNIZING HENS WITH REVERSED CCK-ANTIGEN ON FEED INTAKE (G/24 HR) NEAR PEAK ANTIBODY PROTECTION

| Treatment | n | Feed intake$^1$ g/24 hour | % Birds not consuming |
|---|---|---|---|
| None | 12 | 119 ± 19 | 0 |
| CCK-invert | 12 | 65 ± 18 | 42 |

$^1$mean consumption of 2 birds

TABLE V

EFFECT OF IMMUNIZATION OF LAYING HENS WITH REVERSE CCK ON BODY WEIGHT 3 MONTHS FOLLOWING IMMUNIZATION
(mean + std error)

| Treatment | Body weight (g) | % of hens under 1700 g |
|---|---|---|
| None | 1823 ± 44 | 15 |
| CCK-invert | 1766 ± 35 | 40 |

METHOD III

Outbred mice were fed either the control yolk powder (n=7) or the reverse CCK immune yolk powder (n=8). The dose used was equal to the 5 yolks/3.63 kg feed used in the chick study. Food consumption was depressed in mice fed the reversed CCK immune yolk relative to those fed the control yolk. The depression in food intake was observed within the first 16 hours following the feeding of the immune yolk and return to normal when fed the control yolk. See Tables VI, VII and VIII for results.

TABLE VI

EFFECT OF FEEDING EGG YOLK ANTIBODY TO REVERSED CCK ON MOUSE PERFORMANCE (7 DAYS)

| Treatment | n | Starting weight | Ending weight | Change as % BW |
|---|---|---|---|---|
| Control yolk | 3 | 25.3 ± 2 | 27.0 ± 2 | +7.1 |
| Anti-invert CCK | 3 | 29.8 ± 1 | 31.4 ± 1 | +5.4* | n = 3 cages of outbred mice.
*25% of the mice lost weight. None of the controls lost weight.

TABLE VII

EFFECT OF FEEDING EGG YOLK ANTIBODY TO REVERSED CCK ON MOUSE FEED CONSUMPTION

| Treatment | n | Intake first 24 hours (g) | Intake/m over 7 days (g) |
|---|---|---|---|
| Control yolk | 3 | 11 ± 4 | 10 ± 2 |
| Anti-invert CCK | 3 | 3 ± 1 | 7 ± 1 |

TABLE VIII

CHANGE IN 24-HOUR FOOD CONSUMPTION OF CONTROL MICE SWITCHED TO REVERSE CCK ANTIBODY AND MICE ON REVERSE CCK ANTIBODY SWITCHED TO CONTROL DIET

| Treatment switch | 24 hour change relative to preceding 24 hour (%) | Actual 24-hour consumption |
|---|---|---|
| CCK* to Control | +39 ± 18 | 9.2 ± 3 |
| Control to CCK | −47 ± 22 | 3.8 ± 2 |

*CCK = Antibody to reverse CCK peptide.

---

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 8
        ( B ) TYPE: amino acid
        ( D ) TOPOLOGY: Linear ( i i ) MOLECULE TYPE:
        ( A ) DESCRIPTION: peptide ( i i i ) HYPOTHETICAL: no ( i x ) FEATURE:
        ( A ) NAME/KEY: Reverse choleocystokinin
        ( B ) IDENTIFICATION METHOD: Found by experiment
        ( D ) OTHER INFORMATION: Causes satiety ( x i ) SEQUENCE DESCRIPTION: SEQ ID NO: 1:

Phe Asp Met Trp Gly Met Tyr Asp
1                  5

( 2 ) INFORMATION FOR SEQ ID NO:2:

( i ) SEQUENCE CHARACTERISTICS:
        ( A ) LENGTH: 8
        ( B ) TYPE: amino acid
        ( D ) TOPOLOGY: Linear ( i i ) MOLECULE TYPE:
        ( A ) DESCRIPTION: peptide ( i i i ) HYPOTHETICAL: no ( i x ) FEATURE:

( A ) NAME/KEY: Reverse choleocystokinin
( C ) IDENTIFICATION METHOD: Found by experiment
( D ) OTHER INFORMATION: Tyr 7 has an "-SO3H"group attached;
Causes satiety ( x i ) SEQUENCE DESCRIPTION: SEQ ID NO: 2:

Phe Asp Met Trp Gly Met Tyr Asp
1               5

( 2 ) INFORMATION FOR SEQ ID NO:3:

( i ) SEQUENCE CHARACTERISTICS:
        ( A ) LENGTH: 8
        ( B ) TYPE: amino acid
        ( D ) TOPOLOGY: Linear ( i i ) MOLECULE TYPE:
        ( A ) DESCRIPTION: peptide ( i i i ) HYPOTHETICAL: no ( i x ) FEATURE:
        ( A ) NAME/KEY: Reverse choleocystokinin
        ( C ) IDENTIFICATION METHOD: Found by experiment
        ( D ) OTHER INFORMATION: Asp 8 has "-NH2"group attached;
causes satiety ( x i ) SEQUENCE DESCRIPTION: SEQ ID NO: 3:

Phe Asp Met Trp Gly Met Tyr Asp
1               5

( 2 ) INFORMATION FOR SEQ ID NO:4:

( i ) SEQUENCE CHARACTERISTICS:
        ( A ) LENGTH: 8
        ( B ) TYPE: amino acid
        ( D ) TOPOLOGY: Linear ( i i ) MOLECULE TYPE:
        ( A ) DESCRIPTION: peptide ( i i i ) HYPOTHETICAL: no ( i x ) FEATURE:
        ( A ) NAME/KEY: Reverse choleocystokinin
        ( C ) IDENTIFICATION METHOD: Found by experiment
        ( D ) OTHER INFORMATION: Tyr 7 has "-SO3H"group attached;
Asp has "- NH2"group attached; causes satiety ( x i ) SEQUENCE DESCRIPTION: SEQ ID NO: 4:

Phe Asp Met Trp Gly Met Tyr Asp
1               5

( 2 ) INFORMATION FOR SEQ ID NO:5:

( i ) SEQUENCE CHARACTERISTICS:
        ( A ) LENGTH: 8
        ( B ) TYPE: amino acid
        ( D ) TOPOLOGY: Linear ( i i ) MOLECULE TYPE:
        ( A ) DESCRIPTION: peptide/protein ( i i i ) HYPOTHETICAL: no ( i v ) ANTI-SENSE: no ( i x ) FEATURE:
        ( A ) NAME/KEY: Choleocystokinin
        ( D ) OTHER INFORMATION: Includes conservatively modified
variants thereof; causes satiety ( x i ) SEQUENCE DESCRIPTION: SEQ ID NO: 5:

| | | | | | | | |
|---|---|---|---|---|---|---|---|
| Asp | Tyr | Met | Gly | Trp | Met | Asp | Phe |
| 1 | | | | 5 | | | |

Various modes of carrying out the invention are contemplated as being within the scope of the following claims particularly pointing out and distinctly claiming the subject matter regarded as the invention.

We claim:

1. A method of mimicking the physiological effects of choleocytokinin in an animal comprising:
    administering an antibody to reverse choleocytokinin to said animal wherein said reverse choleocytokinin has an amino acid sequence which is the reverse sequence of choleocytokinin from the amino to the carboxyl ends.

2. The method of claim 1 wherein administering said antibody is via inoculating said animal with said antibody.

3. The method of claim 1 wherein administering said antibody is via feeding said animal with an antibody containing substance.

4. The method of claim 3 wherein said antibody containing substance is obtained from an avian.

5. The method of claim 4 wherein said antibody containing substance is obtained from eggs of said avian.

6. The method of claim 3 wherein said antibody containing substance is obtained from a mammal.

7. The method of claim 3 wherein said antibody containing substance is obtained from whole blood, serum, plasma, or milk.

8. The method of claim 1 wherein administering said antibody is via passive transfer from a dam to said animal wherein said animal is said dam's offspring and said passive transfer occurs during embryonic development.

9. The method of claim 8 wherein said offspring is a cross-offspring.

10. The method of claim 1 wherein said animal is a mammal.

11. The method of claim 10 wherein said mammal is a human.

12. The method of claim 1 wherein said animal is an avian.

13. A method of suppressing appetite in mammals comprising:
    administering to said mammal an antibody to reverse choleocytokinin wherein said reverse choleocytokinin has the reverse amino acid sequence of choleocytokinin.

14. The method of claim 13 wherein said mammal is a human.

15. The method of claim 13 wherein administering said antibody is via inoculating said mammal with said antibody.

16. The method of claim 13 wherein administering said antibody is via feeding said mammal with an antibody containing substance.

17. A method of suppressing appetite in mammals comprising:
    administering to said mammal an antibody specific to reverse CCK peptide.

18. A feed substance for a mammal, comprising:
    an organic meal;
    an appetite-suppressing effective amount of an antibody wherein said antibody is specific to reverse choleocytokinin.

* * * * *